United States Patent [19]

Thurkauf et al.

[11] Patent Number: 5,159,083
[45] Date of Patent: Oct. 27, 1992

[54] CERTAIN AMINOMETHYL PHENYLIMIDAZOLE DERIVATIVES; A CLASS OF DOPAMINE RECEPTOR SUBTYPE SPECIFIC LIGANDS

[75] Inventors: Andrew Thurkauf, Bradford; Alan J. Hutchison, Madison, both of Conn.

[73] Assignee: Neurogen Corporation, Branford, Conn.

[21] Appl. No.: 635,256

[22] Filed: Dec. 28, 1990

[51] Int. Cl.$^5$ .......................................... C07D 233/64
[52] U.S. Cl. ................................................ 548/335.5
[58] Field of Search ........................ 548/337, 342, 343

[56] References Cited

PUBLICATIONS

Ingle et al., J. Pharm. Pharmacol., 15 (9), pp. 620–623. (1963).
Chemical Abstracts, vol. 112, entry 112:178981q, 1990.

Primary Examiner—Patricia L. Morris
Assistant Examiner—Lenora Miltenberger
Attorney, Agent, or Firm—Allegretti & Witcoff, Ltd.

[57] ABSTRACT

This invention encompasses compounds of the formula:

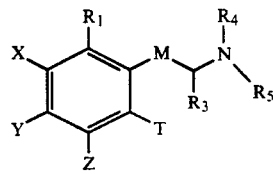

where X, Y, Z, T, $R_1$, $R_3$, $R_4$, and $R_5$ are variables representing various organic and inorganic substituents;

M is

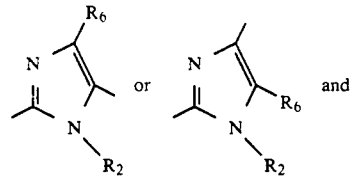

$R_2$ and $R_6$ represent hydrogen or alkyl substituents; or $R_1$ and $R_2$ together may represent $-(CH_2)_{n1}$ where $n_1$ is 1, 2, or 3; or $NR_4R_5$ represents substituted or unsubstituted-tetrahydroisoquinolinyl; or

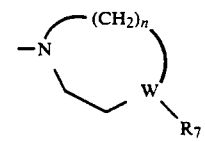

where n is 1, 2, or 3; W is N or CH; and $R_7$ represents hydrogen or aryl; or $W-R_7$ is oxygen or sulfur.

These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Futhermore compounds of this invention may be useful in treating the extraparamidyl side effects associated with the use of conventional neuroleptic agents.

21 Claims, 3 Drawing Sheets

Compound 1

Compound 8

Compound 16

Compound 23

Compound 25

Compound 28

Compound 30

CERTAIN AMINOMETHYL PHENYLIMIDAZOLE DERIVATIVES; A CLASS OF DOPAMINE RECEPTOR SUBTYPE SPECIFIC LIGANDS

BACKGROUND OF THE INVENTION

1. Field of the Invention

This invention relates to certain aminomethyl phenylimidazole derivatives which selectively bind to brain dopamine receptor subtypes. This invention also relates to pharmaceutical compositions comprising such compounds. It further relates to the use of such compounds in treating affective disorders such as schizophrenia and depression as well as certain movement disorders such as Parkinsonism. Furthermore compounds of this invention may be useful in treating the extrapyramidyl side effects associated with the use of conventional neuroleptic agents. The interaction of aminomethyl phenylimidazole derivatives of the invention with dopamine receptor subtypes is described. This interaction results in the pharmacological activities of these compounds.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patients lifetime and can result in prolonged institutionalization. In the US today, approximately 40% of all hospitalized psychiatric patents suffer from schizophrenia.

During the 1950's physicians demonstrated that they could sucessfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least three classes of dopamine receptors appear to mediate the actions of this transmitter. These dopamine receptors differ in their pharmacological specificity and were originally classified upon these differences in the pharmacology of different chemical series. The butyrophenones, containing many potent antipsychotic drugs were quite weak at the dopamine receptor that activated adenylate cyclase (now known as a D1 dopamine receptor). In contrast, they labelled other dopamine receptors (called D2 receptors) in the subnanomolar range and a third type D3 in the nanomolar range. Phenothiazines possess nanomolar affinity for all three types of dopamine receptors. Other drugs have been developed with great specificity for the D1 subtype receptor.

Recently, a new group of drugs (such as sulpiride and clozapine) have been developed with a lesser incidence of extrapyramidal side effects than classical neuroleptics. In addition, there is some indication that they may be more beneficial in treating negative symptoms in some patients. Since all D2 blockers do not possess a similar profile, hypotheses underlying the differences have been investigated. The major differences have been in the anticholinergic actions of the neuroleptics as well as the possibility that the dopamine receptors may differ in motor areas from those in the limbic areas thought to mediate the antipsychotic responses. The existence of the D3 and other as yet undiscovered dopamine receptors may contribute to this profile. Some of the atypical compounds possess similar activity at both D2 and D3 receptors. The examples of this patent fall into this general class of molecules.

Using molecular biological techniques it has been possible to clone cDNAs coding for each of the pharmacologically defined receptors. There are at least two forms of D1, and two forms of D2 dopamine receptors. In addition, there is at least one form of D3 dopamine receptor. Examples from the aminomethyl phenylimidazole series of this patent possess differential affinities for each receptor subtype.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidyl side effects associated with the use of conventional neuroleptic agents. Accordingly, a broad embodiment of the invention is directed to a compound of Formula I:

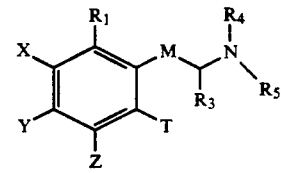

and the pharmaceutically acceptable non-toxic salts thereof wherein $R_1$ and T are the same or different and represent hydrogen, halogen, hydroxy, straight or branched chain lower alkyl having 1–6 carbon atoms, or straight or branched chain lower alkoxy having 1–6 carbon atoms;

M is

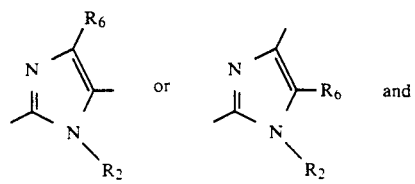

and $R_2$ is hydrogen or straight or branched chain lower alkyl having 1-6 carbon atoms, or $R_1$ and $R_2$ together may represent —$(CH_2)_{n1}$— where $n_1$ is 1, 2, or 3;

X and Z are the same or different and represent hydrogen, halogen, hydroxy, straight or branched chain lower alkyl having 1-6 carbon atoms, straight or branched chain lower alkoxy having 1-6 carbon atoms or $SO_2R_{16}$ or $SO_2NHR_{16}$ where $R_{16}$ is straight or branched chain lower alkyl having 1-6 carbon atoms;

Y is hydrogen, amino, halogen, or straight or branched chain lower alkyl having 1-6 carbon atoms;

$R_3$ is hydrogen or straight or branched chain lower alkyl having 1-6 carbon atoms, or $R_3$ and $R_4$ together may represent —$(CH_2)_{n2}$— where $n_2$ is 2, 3 or 4;

$R_6$ is hydrogen, halogen or straight or branched chain lower alkyl having 1-6 carbon atoms;

$R_4$ and $R_5$ are the same or different and represent hydrogen, straight or branched chain lower alkyl having 1-6 carbon atoms, aryl straight or branched chain lower alkyl having 1-6 carbon atoms or $R_2$ and $R_5$ together may represent —$(CH_2)_{n3}$— where $n_3$ is 2 or 3; or $NR_4R_5$ together represent 2-(1,2,3,4-tetrahydroisoquinolinyl), either unsubstituted or mono or disubstituted with halogen, hydroxy, straight or branched chain lower alkyl having 1-6 carbon atoms, or straight or branched chain lower alkoxy having 1-6 carbon atoms; or $NR_4R_5$ represents

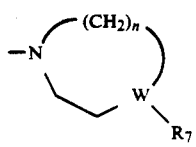

where

W is N or CH;

$R_7$ is hydrogen, phenyl, pyridyl or pyrimidinyl, unsubstituted or mono or disubstituted with halogen, hydroxy, straight or branched chain lower alkyl having 1-6 carbon atoms, or straight or branched chain lower alkoxy having 1-6 carbon atoms; or W—$R_7$ is oxygen or sulfur; and n is 1, 2, or 3.

These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Furthermore compounds of this invention may be useful in treating the extrapyramidyl side effects associated with the use of conventional neurolepticagents.

DETAILED DESCRIPTION OF THE INVENTION

Figure 1A:
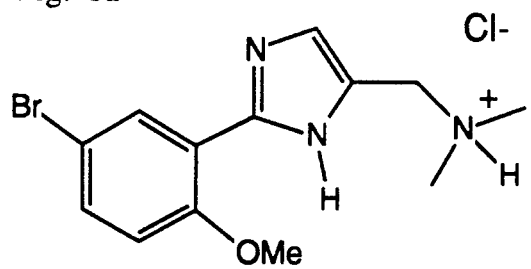
FIGS. 1(a-g) show representative aminomethyl phenylimidazoles of the present invention.
Figure 1B:
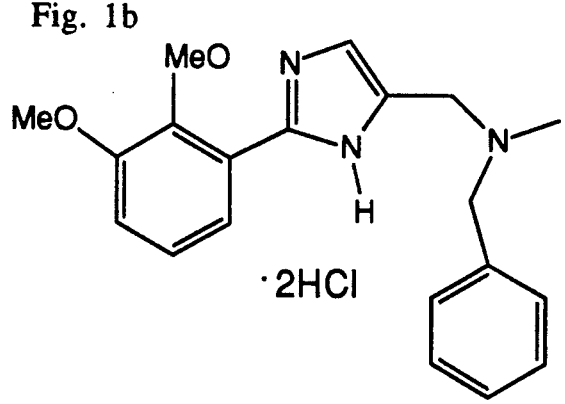
Figure 1C:
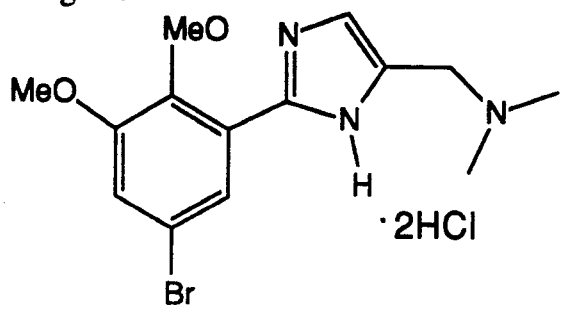
Figure 1D:
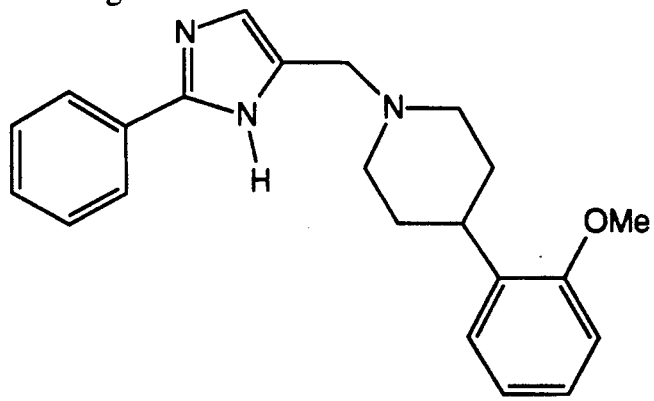
Figure 1E:
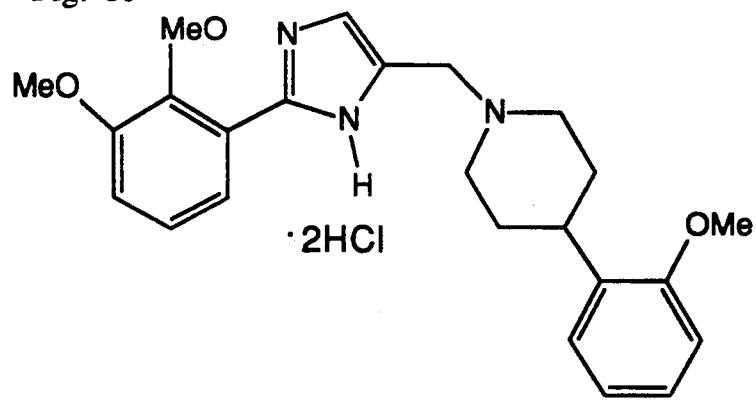
Figure 1F:
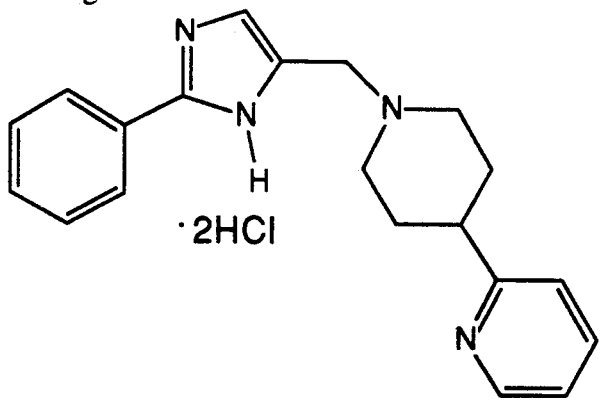
Figure 1G:
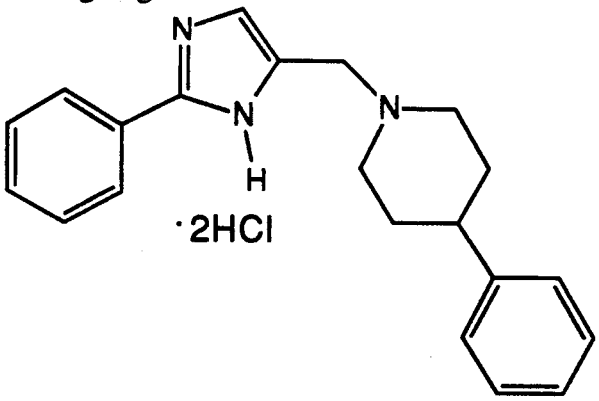

The novel compounds encompassed by the instant invention can be described by general formula I:

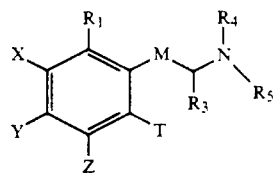

and the pharmaceutically acceptable non-toxic salts thereof wherein $R_1$ and T are the same or different and represent hydrogen, halogen, hydroxy, straight or branched chain lower alkyl having 1-6 carbon atoms, or straight or branched chain lower alkoxy having 1-6 carbon atoms;

M is

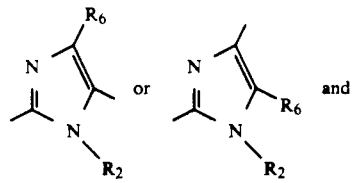

$R_2$ is hydrogen or straight or branched chain lower alkyl having 1-6 carbon atoms, or $R_1$ and $R_2$ together may represent —$(CH_2)_{n1}$— where $_{n1}$ is 1, 2, or 3;

X and Z are the same or different and represent hydrogen, halogen, hydroxy, straight or branched chain lower alkyl having 1-6 carbon atoms, straight or branched chain lower alkoxy having 1-6 carbon atoms or $SO_2R_{16}$ or $SO_2NHR_{16}$ where $R_{16}$ is straight or branched chain lower alkyl having 1-6 carbon atoms;

Y is hydrogen, amino, halogen, or straight or branched chain lower alkyl having 1-6 carbon atoms;

$R_3$ is hydrogen or straight or branched chain lower alkyl having 1-6 carbon atoms, or $R_3$ and $R_4$ together may represent —$(CH_2)_{n2}$— where $n_2$ is 2, 3 or 4;

$R_6$ is hydrogen, halogen or straight or branched chain lower alkyl having 1-6 carbon atoms;

$R_4$ and $R_5$ are the same or different and represent hydrogen, straight or branched chain lower alkyl having 1-6 carbon atoms, aryl straight or branched chain lower alkyl having 1-6 carbon atoms or $R_2$ and $R_5$ together may represent —$(CH_2)_{n3}$— where $n_3$ is 2 or 3; or $NR_4R_5$ together represent 2-(1,2,3,4-tetrahydroisoquinolinyl), either unsubstituted or mono or disubstituted with halogen, hydroxy, straight or branched chain lower alkyl having 1-6 carbon atoms, or straight or branched chain lower alkoxy having 1-6 carbon atoms; or $NR_4R_5$ represents

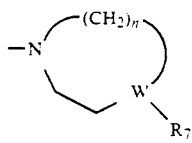

where
W is N or CH;
R$_7$ is hydrogen, phenyl, pyridyl or pyrimidinyl, unsubstituted or mono or disubstituted with halogen, hydroxy, straight or branched chain lower alkyl having 1-6 carbon atoms, or straight or branched chain lower alkoxy having 1-6 carbon atoms; or
W—R$_7$ is oxygen or sulfur; and
n is 1, 2, or 3.

The present invention further encompasses compounds of Formula II:

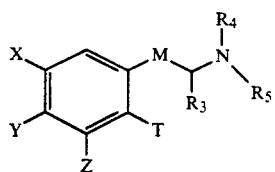

and the pharmaceutically acceptable non-toxic salts thereof wherein
M is

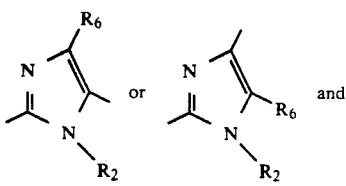

R$_2$ is hydrogen or methyl;
R$_6$ is hydrogen, halogen or straight or branched chain lower alkyl having 1-6 carbon atoms;
X and Z are the same or different and represent hydrogen, halogen, straight or branched chain lower alkyl having 1-6 carbon atoms, or SO$_2$R$_{16}$ or SO$_2$NHR$_{16}$ where R$_{16}$ is straight or branched chain lower alkyl having 1-6 carbon atoms;
Y is hydrogen, amino, or halogen;
T is hydrogen, halogen, hydroxy, or straight or branched chain lower alkoxy having 1-6 carbon atoms;
R$_3$ is hydrogen or straight or branched chain lower alkyl having 1-6 carbon atoms;
R$_4$ and R$_5$ are the same or different and represent hydrogen, straight or branched chain lower alkyl having 1-6 carbon atoms, aryl straight or branched chain lower alkyl having 1-6 carbon atoms or R$_2$ and R$_5$ together may represent —(CH$_2$)$_{n3}$— where n$_3$ is 2 or 3; or
NR$_4$R$_5$ represents

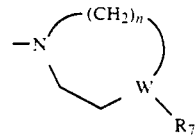

where
W is N or CH;
R$_7$ is hydrogen, phenyl, pyridyl or pyrimidinyl, unsubstituted or mono or disubstituted with halogen, hydroxy, straight or branched chain lower alkyl having 1-6 carbon atoms, or straight or branched chain lower alkoxy having 1-6 carbon atoms; or
W—R$_7$ is oxygen or sulfur; and
n is 1, 2, or 3.

The present invention also encompasses compounds of Formula III:

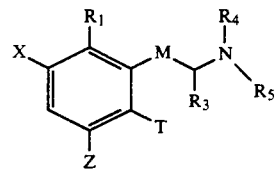

and the pharmaceutically acceptable non-toxic salts thereof wherein
R$_1$ is hydrogen, halogen, hydroxy, straight or branched chain lower alkyl having 1-6 carbon atoms, or straight or branched chain lower alkoxy having 1-6 carbon atoms;
M is

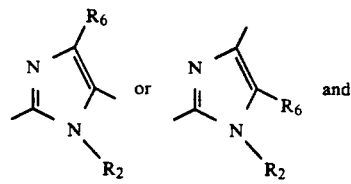

R$_2$ is hydrogen or straight or branched chain lower alkyl having 1-6 carbon atoms, or R$_1$ and R$_2$ together may represent —(CH$_2$)$_{n1}$— where n$_1$ is 1, 2, or 3;
R$_6$ is hydrogen, halogen or straight or branched chain lower alkyl having 1-6 carbon atoms;
X and Z are the same or different and represent hydrogen, halogen, straight or branched chain lower alkyl having 1-6 carbon atoms, or SO$_2$R$_{16}$ or SO$_2$NHR$_{16}$ where R$_{16}$ is straight or branched chain lower alkyl having 1-6 carbon atoms;
T is hydrogen, halogen, hydroxy, or straight or branched chain lower alkoxy having 1-6 carbon atoms;
R$_3$ is hydrogen or straight or branched chain lower alkyl having 1-6 carbon atoms;
R$_4$ and R$_5$ are the same or different and represent hydrogen, straight or branched chain lower alkyl having 1-6 carbon atoms, aryl straight or branched chain lower alkyl having 1-6 carbon atoms or R$_2$ and R$_5$ together may represent —(CH$_2$)$_{n3}$— where n$_3$ is 2 or 3; or
NR$_4$R$_5$ represents

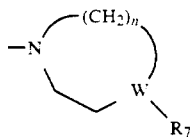

where
W is N or CH;

R$_7$ is hydrogen, phenyl, pyridyl or pyrimidinyl, unsubstituted or mono or disubstituted with halogen, hydroxy, straight or branched chain lower alkyl having 1-6 carbon atoms, or straight or branched chain lower alkoxy having 1-6 carbon atoms; or W—R$_7$ is oxygen or sulfur; and n is 1, 2, or 3.

In addition, the present invention encompasses compounds of Formula IV:

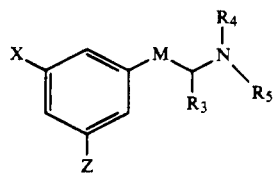

and the pharmaceutically acceptable non-toxic salts thereof wherein

M is

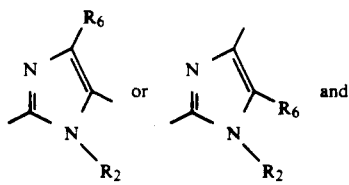

R$_2$ is hydrogen or methyl;

R$_6$ is hydrogen, halogen or straight or branched chain lower alkyl having 1-6 carbon atoms;

X and Z are the same or different and represent hydrogen, halogen, straight or branched chain lower alkyl having 1-6 carbon atoms, or SO$_2$R$_{16}$ or SO$_2$NHR$_{16}$ where R$_{16}$ is straight or branched chain lower alkyl having 1-6 carbon atoms;

R$_3$ is hydrogen or straight or branched chain lower alkyl having 1-6 carbon atoms;

R$_4$ and R$_5$ are the same or different and represent hydrogen, straight or branched chain lower alkyl having 1-6 carbon atoms, aryl straight or branched chain lower alkyl having 1-6 carbon atoms or R$_2$ and R$_5$ together may represent —(CH$_2$)$_{n3}$— where n$_3$ is 2 or 3; or NR$_4$R$_5$ represents

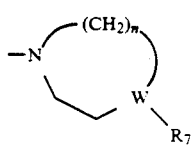

where
W is N or CH;

R$_7$ is hydrogen, phenyl, pyridyl or pyrimidinyl, unsubstituted or mono or disubstituted with halogen, hydroxy, straight or branched chain lower alkyl having 1-6 carbon atoms, or straight or branched chain lower alkoxy having 1-6 carbon atoms; or W—R$_7$ is oxygen or sulfur; and n is 1, 2, or 3.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Representative compounds of the present invention, which are encompassed by Formula I, include, but are not limited to the compounds in FIG. I and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The pharmaceutical utility of compounds of this invention are indicated by the following assays for dopamine receptor subtype affinity.

Assay for D2 and D3 receptor binding activity

Striatal tissue is dissected from adult male Sprague Dawley rats or BHK 293 cells are harvested containing recombinantly produced D2 or D3 receptors. The sample is homogenized in 100 volumes (w/vol) of 0.05M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.5 ml of tissue sample, 0.5 nM 3H-raclopride and the compound of interest in a total incubation of 1.0 ml. Nonspecific binding is defined as that binding found in the presence of 10–4M dopamine; without further additions, nonspecific binding is less than 20% of total binding. The binding characteristics of examples of this patent are shown in Table 1 for Rat Striatal Homogenates.

TABLE I

| Compound Number[1] | IC$_{50}$(uM) |
| --- | --- |
| 1 | 0.900 |
| 8 | 0.011 |
| 16 | 0.014 |
| 23 | 0.100 |
| 25 | 0.018 |
| 28 | 0.620 |
| 30 | 0.200 |

[1]Compound numbers relate to compounds shown in FIG. I.

Compounds 8, 16 and 25 are particularly preferred embodiments of the present invention because of their potency in binding to dopamine receptor subtypes.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occuring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I. Those having skill in the art will recognize that the starting materials may be varied and additional steps employed to produce compounds encompassed by the present invention.

and $R_5$ together may represent —$(CH_2)_{n_3}$— where $n_3$ is 2 or 3; or $NR_4R_5$ represents 2-(1,2,3,4-tetrahydroisoquinolinyl), either unsubstituted or mono or disubstituted with halogen, hydroxy, straight or branched chain lower alkyl having 1-6 carbon atoms, or straight or branched chain lower alkoxy having 1-6 carbon atoms; or $NR_4R_5$ represents

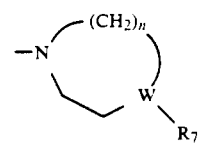

where
W is N or CH;
$R_7$ is hydrogen, phenyl, pyridyl or pyrimidinyl, unsubstituted or mono or disubstituted with Scheme I

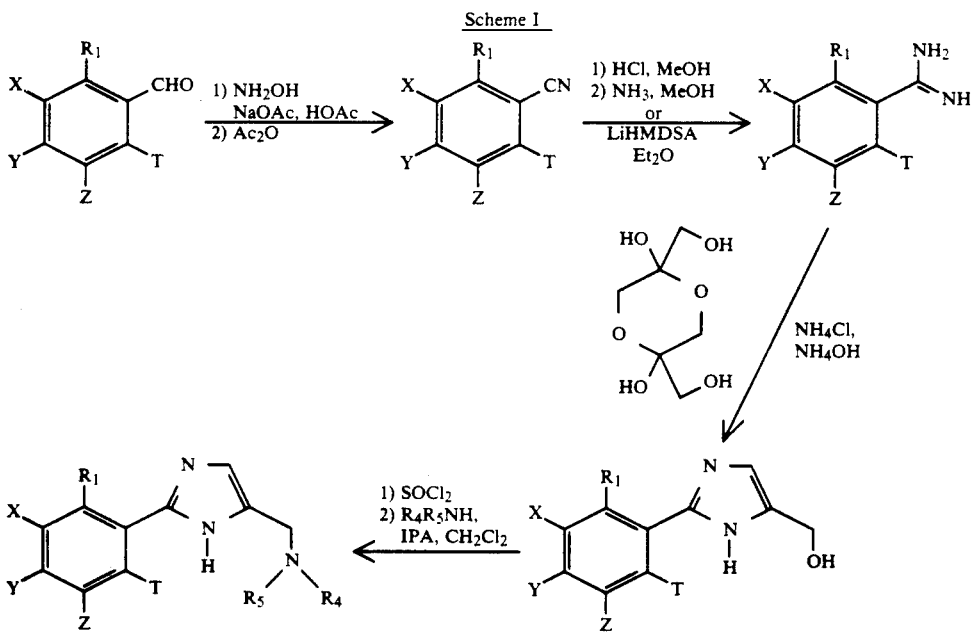

where
$R_1$ and T are the same or different and represent hydrogen, halogen, hydroxy, straight or branched chain lower alkyl having 1-6 carbon atoms, or straight or branched chain lower alkoxy having 1-6 carbon atoms;

X and Z are the same or different and represent hydrogen, halogen, hydroxy, straight or branched chain lower alkyl having 1-6 carbon atoms, straight or branched chain lower alkoxy having 1-6 carbon atoms or $SO_2R_{16}$ or $SO_2NHR_{16}$ where $R_{16}$ is straight or branched chain lower alkyl having 1-6 carbon atoms;

Y is hydrogen, amino, halogen, or straight or branched chain lower alkyl having 1-6 carbon atoms;

$R_4$ and $R_5$ are the same or different and represent hydrogen, straight or branched chain lower alkyl having 1-6 carbon atoms, aryl straight or branched chain lower alkyl having 1-6 carbon atoms or $R_2$ halogen, hydroxy, straight or branched chain lower alkyl having 1-6 carbon atoms, or straight or branched chain lower alkoxy having 1-6 carbon atoms; or $W-R_7$ is oxygen or sulfur; and
n is 1,2, or 3.

The invention is illustrated further by the following examples which are not to be construed as limiting the invention in scope or spirit to the specific procedures and compounds described in them.

EXAMPLE I

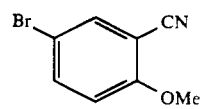

A mixture of 5-Bromo-o-anisaldehyde (6.45 g), hydroxylamine hydrochloride (2.2 g), sodium acetate (4.1 g) and acetic acid (20 mL) was heated at 100° C. with stirring for 1 h. Acetic anhydride was added (20 mL) and the mixture was refluxed for 8 h. The reaction mixture was poured onto ice water and the mixture was made basic by the careful addition of 50% sodium hydroxide. The product was extracted with ether, the ether extracts were dried over magnesium sulfate and the sovent was removed in vacuo. The residue was crystallized from ether/hexane to afford 5-Bromo-2-methoxybenzonitrile.

EXAMPLE II

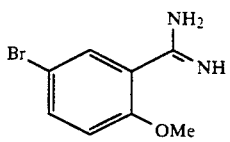

A mixture of 5-Bromo-2-methoxy-benzonitrile (4.0 g), 3A molecular sieves (5 g) and anhydrous methanol (60 mL) was saturated with HCl gas at room temperature and allowed to stand at room temperature for 24 h. The solvent was removed in vacuo and the residue taken up in 75 mL of anhydrous methanol and saturated with ammonia gas at room temperature. The reaction mixture was then heated at 80° C. for 4 h in a sealed tube. The solvent was removed in vacuo, the reaction mixture was diluted with 3N HCl and washed with ethyl acetate to remove unreacted nitrile. The aqueous layer was made basic with 50% NaOH and the product was extracted three times with 10% methanol in methylene chloride. The combined organic extracts were dried over magnesium sulfate and the solvents removed in vacuo to afford 5-Bromo-2-methoxy-benzamidine as a glassy solid.

EXAMPLE III

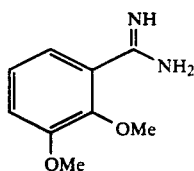

To a solution of 1,1,1,3,3,3-hexamethylsisilazane (20 g) in dry ether (150 mL) was added 2.4M n-butyllithium in hexane (5 mL). After 10 min at room temperature, 2,3-Dimethoxybenzonitrile (16.3 g) was added in one portion and the mixture was kept at room temperature for 16 h. The reaction mixture was the poured onto excess 3N HCl. The aqueous layer was separated, basified with 50% NaOH and the product was extracted three times with 10% methanol in methylene chloride. The combined organic extracts were dried over magnesium sulfate and the solvents removed in vacuo to afford 2,3-Dimethoxy-benzamidine as a glassy solid.

EXAMPLE IV

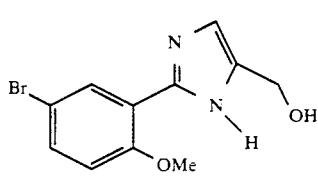

A mixture of 5-Bromo-2-methoxy-benzamidine (1.5 g), 1,3-dihydroxyacetone dimer (1.0 g), ammonium chloride (1.3 g), tetrahydrofuran (3 mL) and con-centrated aqueous ammonium hydroxide (10 mL) was heated at 90° C. for 3 h. The reaction mixture was chilled on ice and the precipitated product was collected and recrystallized from methanol to afford 2-(5-Bromo-2-methoxyphenyl)-5-hydroxymethyl-imidazole as a yellow solid.

EXAMPLE V (Compound 1)

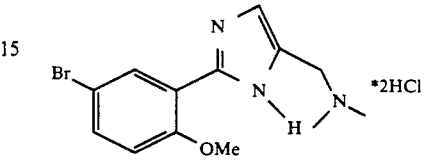

A mixture of 2-(5-Bromo-2-methoxyphenyl)-5-hydroxymethylimidazole (500 mg) and thionyl chloride (1.5 mL) was heated at 80° C. for 1 h. Ether (15 mL) was added and the resulting solid was collected and washed with ether. This solid was added in one portion to a mixture of dimethylamine (3 mL), isopropanol (15 mL) and methylene chloride (30 mL) and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was treated with ethanolic HCl/ether to afford 2-(5-Bromo-2-methoxyphenyl)-4(5)-[(N,N-dimethyl)aminomethyl]-imidazole dihydrochloride (Compound 1) melting at 242°-243° C.

EXAMPLE VI

The following compounds were prepared essentially according to the procedure described in Examples I-V:

(a) 2-Phenyl-4(5)-[(N,N-dimethyl)aminomethyl]-imidazole dihydrochloride (Compound 2) melting at 259°-260° C.

(b) 2-Phenyl-4(5)-(piperidinomethyl)-imidazole dihydrochloride (Compound 3) melting at 245°-247° C.

(c) 2-Phenyl-4(5)-[(N-methyl-N-benzyl)aminomethyl]-imidazole dihydrochloride (Compound 4) melting at 239°-240° C.

(d) 2-(2-Methoxyphenyl)-4(5)-[(N,N-dimethyl)aminomethyl]-imidazole dihydrochloride (Compound 5) melting at 115°-117° C.

(e) 2-(3-Methoxyphenyl)-4(5)-[(N-methyl-N-benzyl)aminomethyl]-imidazole dihydrochloride (Compound 6) melting at 239°-241° C.

(f) 2-(2,3-Dimethoxyphenyl)-4(5)-[(N,N-dimethyl)aminomethyl]-imidazole dihydrochloride (Compound 7) melting at 220°-221° C.

(g) 2-(2,3-Dimethoxyphenyl)-4(5)-[(N-methyl-N-benzyl)aminomethyl]-imidazole dihydrochloride (Compound 8) melting at 200°-202° C.

(h) 2-(3-Methoxyphenyl)-4(5)-[(N,N-diethyl)aminomethyl]-imidazole dihydrochloride (Compound 9) melting at 213°-214° C.

(i) 2-(3-Fluorophenyl)-4(5)-[(N,N-dimethyl)aminomethyl]-imidazole dihydrochloride (Compound 10) melting at 211°-214° C.

(j) 2-(2-Fluorophenyl)-4(5)-[(N-methyl-N-benzyl)aminomethyl]-imidazole dihydrochloride (Compound 11) melting at 241°-244° C.

(k) 2-(3-Methylphenyl)-4(5)-[(N,N-dimethyl)aminomethyl]-imidazole dihydrochloride (Compound 12) melting at 231°-234° C.

(l) 2-(2-Fluorophenyl)-4(5)-[(N,N-dimethyl)aminomethyl]-imidazole dihydrochloride (Compound 13) melting at 246°-247° C.

(m) 2-(4-Fluorophenyl)-4(5)-[(N-methyl-N-benzyl)aminomethyl]-imidazole dihydrochloride (Compound 14) melting at 237°-239° C.

(n) 2-(2-Methoxyphenyl)-4(5)-[(N-methyl-N-benzyl)aminomethyl]-imidazole dihydrochloride (Compound 15) melting at 239°-241° C.

(o) 2-(5-Bromo-2,3-dimethoxyphenyl)-4(5)-[(N,N-dimethyl)aminomethyl]-imidazole dihydrochloride (Compound 16) melting at 194°-196° C.

(p) 2-(5-Bromo-2-methoxyphenyl)-4(5)-[(N-methyl-N-benzyl)aminomethyl]-imidazole dihydrochloride (Compound 17) melting at 169°-172° C.

(q) 2-(5-Bromo-2,3-dimethoxyphenyl)-4(5)-[(N-methyl-N-benzyl)aminomethyl]-imidazole dihydrochloride (Compound 18) melting at 205°-206° C.

(r) 2-(5-Chloro-2-methoxyphenyl)-4(5)-[(N-methyl-N-benzyl)aminomethyl]-imidazole (Compound 19).

(s) 2-(3-Methoxyphenyl)-4(5)-[(N-methyl)aminomethyl]-imidazole dihydrochloride (Compound 20) melting at 208°-209° C.

(t) 4,5-Dihydro-2-(N,N-dimethyl)aminomethyl-imidazo[2,1-a]isoquinoline (Compound 21).

(u) 4,5-Dihydro-2-(N-methyl-N-benzyl)aminomethyl-imidazo[2,1-a]isoquinoline (Compound 22).

EXAMPLE VII

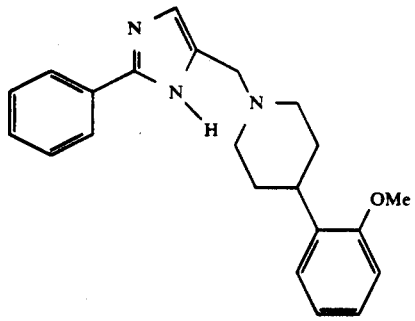

(Compound 23)

A mixture of 2-Phenyl-5-hydroxymethyl-imidazole (350 mg) and thionyl chloride (1 mL) was heated at 80° C. for 1 h. The excess thionyl chloride was removed in vacuo and the residue was dissolved in 20 mL of methylene chloride. This solution was added to a mixture of triethylamine (1 mL) and 1-(2-methoxyphenyl)-piperazine (410 mg) in methylene chloride (20 mL) and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was crystallized from ethyl acetate to afford 2-Phenyl-4(5)-[(4-(2-methoxyphenyl)-piperazin-1-yl)-methyl]-imidazole (Compound 23) melting at 105°-107° C.

EXAMPLE VIII

The following compounds were prepared essentially according to the procedure described in Example VII:

(a) 2-(4-Fluorophenyl)-4(5)-[(4-(2-methoxyphenyl)-piperazin-1-yl)-methyl]-imidazole (Compound 24) melting at 95°-97° C.

(b) 2-(2,3-Dimethoxyphenyl)-4(5)-[(4-(2-methoxyphenyl)-piperazin-1-yl)-methyl]-imidazole dihydrochloride (Compound 25) melting at 217°-218° C.

(c) 2-(3-Chlorophenyl)-4(5)-[(4-(2-methoxyphenyl)-piperazin-1-yl)-methyl]-imidazole dihydrochloride (Compound 26) melting at 198°-199° C.

(d) 2-Phenyl-4(5)-[(4-(2-pyrimidinyl)-piperazin-1-yl)-methyl]-imidazole dihydrochloride (Compound 27) melting at 246°-248° C.

(e) 2-Phenyl-4(5)-[(4-(2-pyridyl)-piperazin-1-yl)-methyl]-imidazole dihydrochloride (Compound 28) melting at 176°-177° C.

(f) 2-Phenyl-4(5)-[(4-benzyl-piperidin-1-yl)-methyl]-imidazole dihydrochloride (Compound 29) melting at 234°-236° C.

(g) 2-Phenyl-4(5)-[(4-phenyl-piperidin-1-yl)-methyl]-imidazole dihydrochloride (Compound 30) melting at 238°-240° C.

(h) 2-Phenyl-4(5)-[(1,2,3,4-tetrahydroisoquinolin)-2-yl-methyl]-imidazole dihydrochloride (Compound 31) melting at 205°-207° C.

EXAMPLE VIV

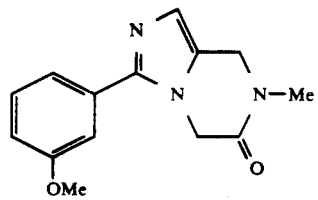

A mixture of 2-(3-Methoxyphenyl)-4(5)-[(N-methyl)aminomethyl]-imidazole (86 mg) chloroacetyl chloride (46 mg) and diisopropylethylamine (100 mg) in tetrahydrofuran (1 mL) was kept at room temperature for 30 min. Dimethylformamide (4 mL) and potassium carbonate (200 mg) was added and the mixture was stirred at room temperature for 10 h. The reaction mixture was diluted with water and the product was extracted with methylene chloride. The solvent was dried over magnesium sulfate and the solvent was removed in vacuo to afford 3-(3-Methoxyphenyl)-7-methyl-5,6,7,8-tetrahydro-imidazo[1,5-a]pyrazin-6-one melting at 115°-117° C. after trituration with ether.

EXAMPLE X

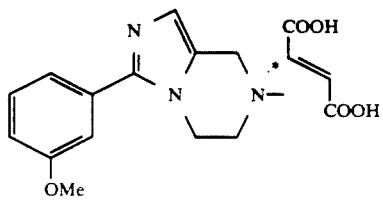

A mixture of 3-(3-Methoxyphenyl)-7-methyl-5,6,7,8-tetrahydroimidazo[1,5-a]pyrazin-6-one (65 mg) and 1N lithium aluminum hydride in tetrahydrofuran (2 mL) in tetrahydrofuran (4 mL) was kept at room temperature for 45 min. After quenching the reaction with 2N sodium hydroxide the reaction was filtered through celite and the solvent was removed in vacuo. The residue was subjected to flash chromatography on silica gel with 5% methanol in chloroform as the eluent to afford 3-(3-Methoxyphenyl)-7-methyl-7,8-dihydro-imidazo[1,5-a]pyrazine followed by 3-(3-Methoxyphenyl)-7-methyl-5,6,7,8-tetrahydro-imidazo[1,5-a]pyrazine whose mono fumarate salt (Compound 32) was crystallized from ethanol/ether and melted at 211°–214°.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

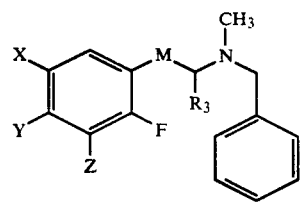

and the pharmaceutically acceptable non-toxic salts thereof wherein:

M is

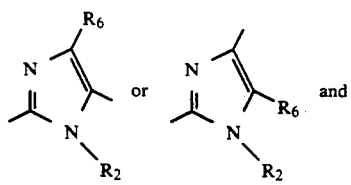

$R_2$ is hydrogen or methyl;

$R_6$ is hydrogen, halogen or straight or branched chain lower alkyl having 1–6 carbon atoms;

X and Z are the same or different and represent hydrogen, halogen, straight or branched chain lower alkyl having 1–6 carbon atoms or $SO_2R_{16}$ or $SO_2NHR_{16}$ where $R_{16}$ is straight or branched chain lower alkyl having 1–6 carbon atoms;

Y is hydrogen, amino, or halogen; and $R_3$ is hydrogen, or straight or branched chain lower alkyl having 1–6 carbon atoms.

2. A compound of the formula:

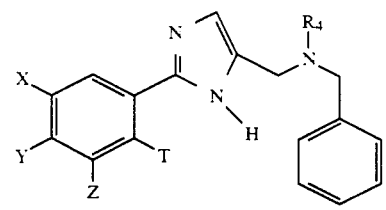

and the pharmaceutically acceptable non-toxic salts thereof wherein:

X is hydrogen, chlorine, or bromine;
Y is hydrogen or fluorine;
Z is hydrogen, methyl, methoxy, or fluorine;
T is hydrogen, methoxy or fluorine; and
$R_4$ is hydrogen, methyl, ethyl, or benzyl.

3. A compound of the formula:

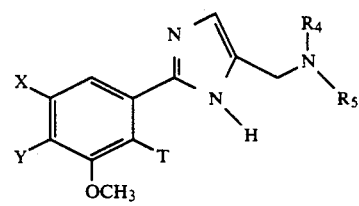

and the pharmaceutically acceptable non-toxic salts thereof wherein:

X is hydrogen, chlorine, or bromine;
Y is hydrogen or fluorine;
T is hydrogen, methoxy; or fluorine
$R_4$ is hydrogen, methyl, ethyl, or benzyl; and
$R_5$ is methyl, ethyl, or benzyl.

4. A compound according to claim 2 which is 2-(5-Bromo-2-methoxyphenyl)-4(5)-[(N,N-dimethyl)aminomethyl]-imidazole dihydrochloride.

5. A compound according to claim 2 which is 2-Phenyl-4(5)-[(N-methyl-N-benzyl)aminomethyl]-imidazole dihydrochloride.

6. A compound which is 2-(2-Methoxyphenyl)-4(5)-[(N,N-dimethyl)aminomethyl]-imidazole dihydrochloride.

7. A compound according to claim 2 which is 2-(3-Methoxyphenyl)-4(5)-[(N-methyl-N-benzyl)aminomethyl]-imidazole dihydrochloride.

8. A compound according to claim 3 which is 2-(2,3-Dimethoxyphenyl)-4(5)-[(N,N-dimethyl)aminomethyl]-imidazole dihydrochloride.

9. A compound according to claim 2 which is 2-(2,3-Dimethoxyphenyl)-4(5)-[(N-methyl-N-benzyl)aminomethyl]-imidazole dihydrochloride.

10. A compound according to claim 3 which is 2-(3-Methoxyphenyl)-4(5)-[(N,N-diethyl)aminomethyl]-imidazole dihydrochloride.

11. A compound which is 2-(3-Fluorophenyl)-4(5)-[(N,N-dimethyl)aminomethyl]-imidazole dihydrochloride.

12. A compound according to claim 2 which is 2-(2-Fluorophenyl)-4(5)-[(N-methyl-N-benzyl)aminomethyl]-imidazole dihydrochloride.

13. A compound which is 2-(3-Methylphenyl)-4(5)-[(N,N-dimethyl)aminomethyl]-imidazole dihydrochloride.

14. A compound which is 2-(2-Fluorophenyl)-4(5)-[(N,N-dimethyl)aminomethyl]-imidazole dihydrochloride.

15. A compound according to claim 2 which is 2-(4-Fluorophenyl)-4(5)-[(N-methyl-N-benzyl)aminomethyl]-imidazole dihydrochloride.

16. A compound according to claim 2 which is 2-(2-Methoxyphenyl)-4(5)-[(N-methyl-N-benzyl)aminomethyl]-imidazole dihydrochloride.

17. A compound according to claim 3 which is 2-(5-Bromo-2,3-dimethoxyphenyl)-4(5)-[(N,N-dimethyl)aminomethyl]-imidazole dihydrochloride.

18. A compound according to claim 2 which is 2-(5-Bromo-2-methoxyphenyl)-4(5)-[(N-methyl-N-benzyl)aminomethyl]-imidazole dihydrochloride.

19. A compound according to claim 2 which is 2-(5-Bromo-2,3-dimethoxyphenyl)-4(5)-[(N-methyl-N-benzyl)aminomethyl]-imidazole dihydrochloride.

20. A compound according to claim 2 which is 2-(5-Chloro-2-methoxyphenyl)-4(5)-[(N-methyl-N-benzyl)aminomethyl]-imidazole.

21. A compound according to claim 3 which is 2-(3-Methoxyphenyl)-4(5)-[(N-methyl)aminomethyl]-imidazole dihydrochloride.

* * * * *